United States Patent
Fadler et al.

(10) Patent No.: US 7,278,785 B2
(45) Date of Patent: Oct. 9, 2007

(54) ADJUSTABLE X-RAY SYSTEM

(75) Inventors: Franz Fadler, Hetzles (DE); Udo Heinze, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 148 days.

(21) Appl. No.: 10/964,273

(22) Filed: Oct. 12, 2004

(65) Prior Publication Data
US 2005/0094770 A1 May 5, 2005

(30) Foreign Application Priority Data
Oct. 14, 2003 (DE) ................. 103 47 734

(51) Int. Cl.
*H05G 1/02* (2006.01)
(52) U.S. Cl. .................................... 378/197
(58) Field of Classification Search ........ 378/193–198, 378/94
See application file for complete search history.

(56) References Cited

U.S. PATENT DOCUMENTS

| | | | |
|---|---|---|---|
| 5,930,328 A * | 7/1999 | Nakamura et al. ............ 378/91 |
| 6,213,638 B1 | 4/2001 | Rattner ........................ 378/198 |
| 6,409,381 B1 * | 6/2002 | Siebenhaar et al. ......... 378/197 |
| 6,764,217 B2 * | 7/2004 | Yasuda et al. ............... 378/205 |

FOREIGN PATENT DOCUMENTS

| DE | 42 37 013 A1 | 5/1994 |
|---|---|---|
| DE | 102 00 534A-1 | 7/2003 |

* cited by examiner

*Primary Examiner*—Jurie Yun
(74) *Attorney, Agent, or Firm*—Brinks Hofer Gilson & Lione

(57) ABSTRACT

An X-ray system, having an adjustable C-arm configured with two degrees of freedom, comprises a memory configured to memorize a travel distance of the C-arm. Via the memory, an adjustability of the C-arm is determined by the memorized travel distance.

17 Claims, 1 Drawing Sheet

ADJUSTABLE X-RAY SYSTEM

FIELD

The invention relates to X-ray systems, and more particularly, to an X-ray system with an adjustable C-arm, which has two degrees of freedom, generally one in an angular direction and one in an orbital direction.

BACKGROUND

An X-ray system of this kind is known for instance from German Patent Disclosure DE 42 37 013 A1. A C-arm of an X-ray system is typically moved from a first position to a second position by manual actuation. Both orbital and angular adjustments of the C-arm, which can be described by two degrees of freedom, are possible. During the adjustment, the C-arm is monitored by an operator for potential collision. If the C-arm is moved back from the second position to the first position, this means the same effort is involved as for the initial movement operation.

SUMMARY

The present invention is defined by the appended claims. This description summarizes some aspects of the present embodiments and should not be used to limit the claims.

One object is to simplify the operation of a C-arm X-ray system, especially for medical applications.

This X-ray system includes an adjustable C-arm that has two degrees of freedom. In the adjustment of the C-arm, a travel distance can be ascertained via a memory. If another adjustment of the C-arm is intended, but in an opposite direction, then the adjustability of the C-arm can be limited to the travel distance of the previous memorized adjustment, or in other words, the adjustability of the C-arm can be reduced to a single degree of freedom. As such, a manual operation may be utilized to approach positions of the C-arm again in which the C-arm was located in the first or initial memorized travel distance. As a result, checking again for the possibility of collision is no longer necessary. The return of the C-arm to a previous position is thus performed not only with a substantially high precision but also in a substantially time-saving way.

To adjust the C-arm, a motor support, a servo support for example, is preferably contemplated. This motor support makes it simple to combine a restriction as needed of the adjustability of the C-arm to a previously memorized travel distance with a control of the motor adjustment of the C-arm. An operator control handle for adjusting the C-arm is preferably disposed on the C-arm, or on some part mechanically connected to it, such as in the form of a so-called railing which may replace a conventional handle of a C-arm that is not adjustable with the motor support.

In one feature, the memory is intended for storing at least one working position, forming one point of the travel distance, of the C-arm in memory. Preferably, the C-arm can be automatically fixed in the working position. Upon adjustment of the C-arm along the memorized travel distance, the C-arm may stop automatically in an exactly defined position upon reaching the working position.

One advantage is that a C-arm of an X-ray system can be adjusted simply and in a time-saving way, semi-automatically, along an arbitrary, previously memorized travel distance.

Illustrative and exemplary embodiments of the invention are described in further detail below with reference to and in conjunction with the figures.

DETAILED DESCRIPTION OF DRAWINGS

Figure 1:
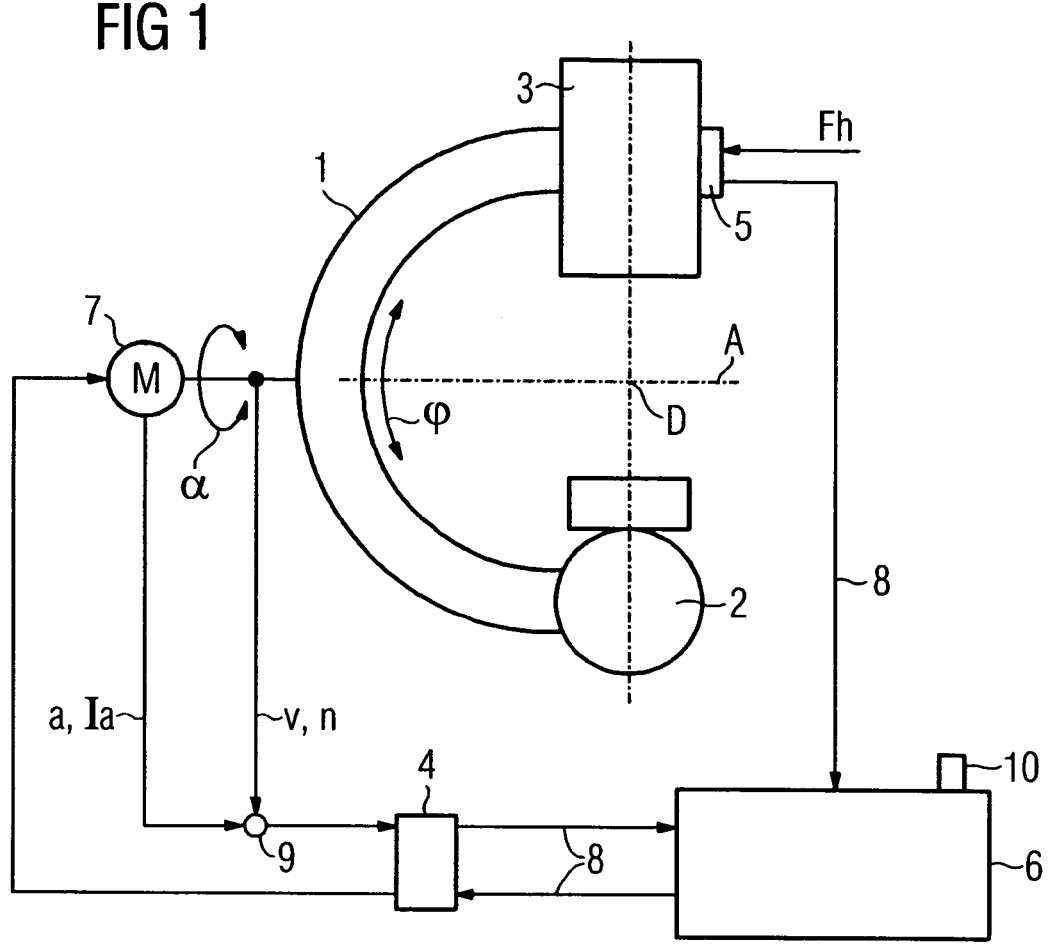
FIG. 1 illustrates schematically an embodiment of a C-arm X-ray system.

Parts and parameters corresponding to one another are identified by the same reference numerals in both drawings.

FIG. 1 symbolically shows an X-ray system with a C-arm 1, to which an X-ray emitter 2 is secured on one end of the arm and a picture-taking system 3 is secured on another end of the arm. The C-arm 1 is adjustable in the angular direction, defined by an angular angle $\alpha$, and in the orbital direction, defined by an orbital angle $\omega$. An associated axis of rotation is marked A and an associated pivot point is marked D. With the angular and orbital adjustment capabilities, the C-arm 1 has two degrees of freedom.

A handle 5, also called a servo railing, is disposed as an operator control handle on the picture-taking system 3. The handle 5 may serve the purpose of manual, servo-supported adjustment of the C-arm 1, including the X-ray emitter 2 and the picture-taking system 3. The operator control handle 5 cooperates, regardless of its geometric design, with force and/or travel pickups that detect the amount and direction of an actuating force Fh and carry a corresponding electrical signal to a closed-loop control unit 6.

The closed-loop control unit 6 may form part of a servo drive of the C-arm 1 and may serve to trigger an electric motor 7, such that the C-arm 1 is adjustable about the pivot point D. The closed-loop control unit 6 is connected to the electric motor 7 and the C-arm 1 via lines 8. Transmitted signals may pertain to an acceleration a of the X-ray system 1, 2, 3; to tan armature current la of the electric motor 7; to s speed v of the X-ray system 1, 2, 3; and/or to an rpm n of the electric motor 7. A comparator 9 may be connected on an input side of the closed-loop control unit 6. A memory 4 may also be linked with the closed-loop control unit 6 but, in a departure from the symbolic representation shown, may also be integrated with the closed-loop control unit 6. The memory 4 serves to record one or more travel distances of the C-arm 1. Via an input device 10, which may be embodied for instance as a button on a control unit or as a foot switch, a so-called pathfinder function of the closed-loop control unit 6 can be activated by which a further adjustment of the C-arm 1 is restricted to the previous travel distance, optionally limited to a defined travel path or a defined travel angle.

A function of the storage in memory and definition of the travel distance of the C-arm 1 will now be described in further detail, referring to FIG. 2.

Figure 2:
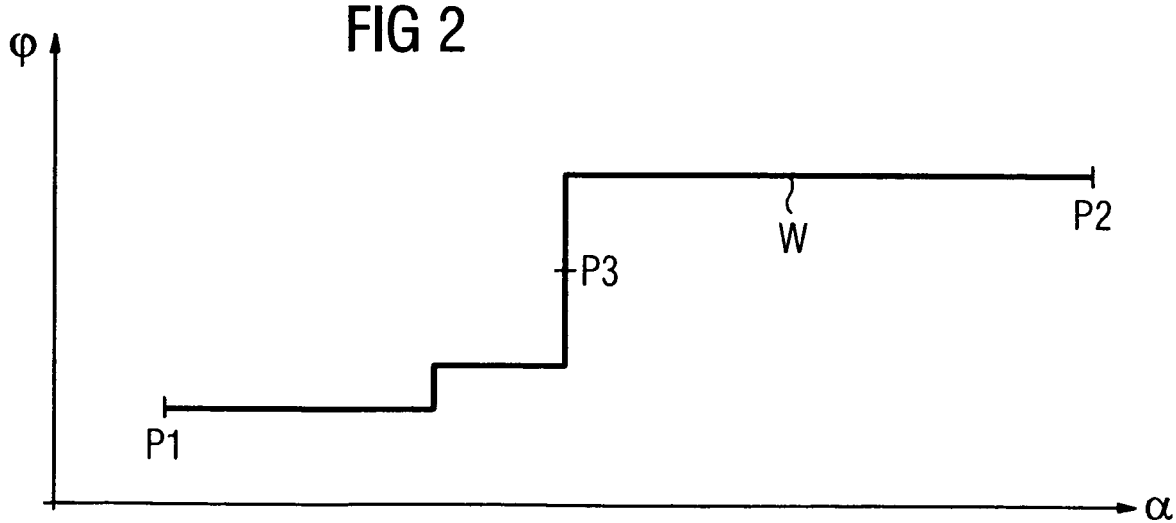
FIG. 2 is a schematic graph illustrating adjustment capabilities of the C-arm of the X-ray system of FIG. 1.

Referring to FIG. 2, the positioning of the C-arm 1 is determined by the angular angle $\alpha$ and the orbital angle $\omega$. Hence the adjustment capabilities of the C-arm 1 can be described by two degrees of freedom. A first position is marked P1 and a second position is marked P2. The C-arm 1 is moved from the first position P1 to the second position P2 over a travel distance W. The travel distance W is stored in the memory 4 during the travel. When the second position P2 is reached, the operator presses the button 10. This operator action limits further adjustment capability of the C-arm 1 to the memorized travel distance W. Hence the C-arm 1 can be moved back into the position P1 or into an arbitrary other position along the travel distance W exactly along the way over which it was previously moved from the position P1 into the position P2. The return of the C-arm 1 along the travel distance W takes place semi-automatically, or in other words with servo support via the actuation handle 5. In the graph of FIG. 2, the C-arm 1 executes solely either an angular or an orbital motion. However, arbitrary motions with angular and orbital components may equally well be executed. An arbitrary position along the travel distance W, and in particular the first position P1 or the second position P2 but an intermediate position P3 is also possible, can be stored as a working position. When the C-arm 1 along the travel distance W reaches the working position P1, P2, P3; these working positions may be indicated to the operator or user, for instance visually. In addition or as an alternative, an operating mode is preferably provided in which the C-arm 1 is automatically stopped upon reaching one of the working positions P1, P2, P3. A working position P1, P2, P3 once stored in memory can thus be found again substantially simply and quickly by the user. All the restrictions to the adjustment capabilities of the C-arm 1 that are described here can be rescinded again as needed in any arbitrary position.

The invention claimed is:

1. An X-ray system, having an adjustable C-arm configured with two degrees of freedom, the system comprising:
   a memory configured to memorize a travel distance of the C-arm, and
   a controller operable to adjust the C-arm based on the memorized travel distance.

2. The X-ray system of claim 1, wherein the C-arm is adjustable via a motorized support.

3. The X-ray system of claim 2, further comprising an operator control handle connected mechanically to the C-arm.

4. The X-ray system of claim 3, wherein a working position of the C-arm is stored in the memory.

5. The X-ray system of claim 4, wherein the C-arm is automatically adjusted to the memorized working position.

6. The X-ray system of claim 2, wherein a working position of the C-arm is stored in the memory.

7. The X-ray system of claim 6, wherein the C-arm is automatically adjusted to the memorized working position.

8. The X-ray system of claim 1, further comprising an operator control handle connected mechanically to the C-arm.

9. The X-ray system of claim 8, wherein a working position of the C-arm is stored in the memory.

10. The X-ray system of claim 9, wherein the C-arm is automatically adjusted to the memorized working position.

11. The X-ray system of claim 1, wherein a working position of the C-arm is stored in the memory.

12. The X-ray system of claim 11, wherein the C-arm is automatically adjusted to the memorized working position.

13. An X-ray system comprising:
   an adjustable C-arm operable in at least two degrees of freedom;
   a memory operable to memorize a path of travel of the C-arm; and
   a controller operable to adjust the C-arm based on the memorized path of travel,
   wherein an adjustability of the C-arm is limited by the memorized path of travel.

14. The X-ray system of claim 13, wherein a working position of the C-arm is stored in the memory.

15. The X-ray system of claim 14, wherein the C-arm is automatically adjusted to the memorized working position.

16. The X-ray system of claim 13, wherein the C-arm is adjustable via a motorized support.

17. The X-ray system of claim 13, further comprising an operator control handle connected mechanically to the C-arm.

* * * * *